(12) United States Patent
Ma et al.

(10) Patent No.: US 9,750,925 B2
(45) Date of Patent: Sep. 5, 2017

(54) PORTED CATHETER ADAPTER HAVING COMBINED PORT AND BLOOD CONTROL VALVE WITH VENTING

(71) Applicant: Becton, Dickinson and Company, Franklin Lakes, NJ (US)

(72) Inventors: Yiping Ma, Layton, UT (US); Weston F. Harding, Lehi, UT (US); Siddarth K. Shevgoor, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 67 days.

(21) Appl. No.: 14/597,027

(22) Filed: Jan. 14, 2015

(65) Prior Publication Data
US 2015/0202421 A1    Jul. 23, 2015

Related U.S. Application Data

(60) Provisional application No. 61/929,708, filed on Jan. 21, 2014.

(51) Int. Cl.
*A61M 39/06* (2006.01)
*A61M 25/06* (2006.01)
(Continued)

(52) U.S. Cl.
CPC ............ *A61M 39/06* (2013.01); *A61M 25/00* (2013.01); *A61M 25/0009* (2013.01);
(Continued)

(58) Field of Classification Search
CPC .... A61M 39/04; A61M 39/045; A61M 39/06; A61M 39/0613; A61M 39/0693; A61M 39/22; A61M 39/26; A61M 2039/062; A61M 2039/0633; A61M 2039/064; A61M 2039/066; A61M 2039/0673; A61M 2039/1072; A61M 2039/2433;
(Continued)

(56) References Cited

U.S. PATENT DOCUMENTS

| | | | |
|---|---|---|---|
| 4,387,879 A | 6/1983 | Tauschkinshi | |
| 4,449,693 A | 5/1984 | Gereg | |

(Continued)

FOREIGN PATENT DOCUMENTS

| | | | |
|---|---|---|---|
| CA | 2 133 053 A1 | 3/1995 | |
| DE | 10 2008 044296 A1 | 7/2010 | |

(Continued)

*Primary Examiner* — Imani Hayman
*Assistant Examiner* — James D Ponton
(74) *Attorney, Agent, or Firm* — Jeanne Luksavage; Craig Metcalf; Kirkton McConkie

(57) ABSTRACT

A ported catheter adapter having a combined blood control valve and port valve, wherein the combined valve comprises one or more vents that permit the passage of air and prevent the passage of fluids. The one or more vents are located on the outer surface of the valve so as to avoid being overlapped with the pathway of the side port. As such, fluid communication between the side port and the vents is prevented. Various venting configurations are provided. The invention further includes a valve actuator that is advanced through a slit in the membrane of the valve to provide a pathway for fluid to bypass the valve.

18 Claims, 13 Drawing Sheets

(51) Int. Cl.
*A61M 39/10* (2006.01)
*A61M 39/24* (2006.01)
*A61M 25/00* (2006.01)
*A61M 39/00* (2006.01)
*A61M 39/02* (2006.01)
*A61M 39/22* (2006.01)
*A61M 39/26* (2006.01)

(52) U.S. Cl.
CPC .... *A61M 25/0097* (2013.01); *A61M 25/0606* (2013.01); *A61M 39/00* (2013.01); *A61M 39/02* (2013.01); *A61M 39/0693* (2013.01); *A61M 39/10* (2013.01); *A61M 39/22* (2013.01); *A61M 39/24* (2013.01); *A61M 39/26* (2013.01); *A61M 2039/062* (2013.01); *A61M 2039/2493* (2013.01); *A61M 2039/266* (2013.01)

(58) Field of Classification Search
CPC .... A61M 2039/2493; A61M 2039/266; A61M 25/01; A61M 25/0105; A61M 25/0169; A61M 25/0172
See application file for complete search history.

(56) References Cited

U.S. PATENT DOCUMENTS

| | | | |
|---|---|---|---|
| 4,758,225 A | 7/1988 | Cox et al. | |
| 4,773,552 A | 9/1988 | Boege et al. | |
| 4,781,702 A | 11/1988 | Herrli | |
| 4,809,679 A | 3/1989 | Shimonaka et al. | |
| 4,842,591 A | 6/1989 | Luther | |
| 4,874,377 A | 10/1989 | Newgard et al. | |
| 4,917,668 A | 4/1990 | Haindl | |
| 4,935,010 A | 6/1990 | Cox et al. | |
| 4,950,257 A | 8/1990 | Hibbs et al. | |
| 5,041,097 A | 8/1991 | Johnson | |
| 5,053,014 A | 10/1991 | Van Heugten | |
| 5,062,836 A | 11/1991 | Wendell | |
| 5,064,416 A | 11/1991 | Newgard et al. | |
| 5,084,023 A | 1/1992 | Lemieux | |
| 5,085,645 A | 2/1992 | Purdy et al. | |
| 5,098,405 A | 3/1992 | Peterson et al. | |
| 5,108,374 A | 4/1992 | Lemieux | |
| 5,127,905 A | 7/1992 | Lemieux | |
| 5,154,703 A | 10/1992 | Bonaldo | |
| 5,156,596 A | 10/1992 | Balbierz et al. | |
| 5,176,652 A | 1/1993 | Littrell | |
| 5,234,410 A | 8/1993 | Graham et al. | |
| 5,269,771 A | 12/1993 | Thomas et al. | |
| 5,290,246 A | 3/1994 | Yamamoto et al. | |
| 5,295,969 A | 3/1994 | Fischell et al. | |
| 5,330,435 A | 7/1994 | Vaillancourt | |
| 5,350,363 A | 9/1994 | Goode et al. | |
| 5,352,205 A | 10/1994 | Dales et al. | |
| 5,405,323 A | 4/1995 | Rogers et al. | |
| 5,456,675 A | 10/1995 | Wolbring et al. | |
| 5,474,544 A | 12/1995 | Lynn | |
| 5,487,728 A | 1/1996 | Vaillancourt | |
| 5,520,666 A | 5/1996 | Choudhury et al. | |
| 5,549,566 A | 8/1996 | Elias et al. | |
| 5,549,577 A | 8/1996 | Siegel et al. | |
| 5,575,769 A | 11/1996 | Vaillancourt | |
| 5,613,663 A | 3/1997 | Schmidt et al. | |
| 5,651,772 A | 7/1997 | Arnett | |
| 5,657,963 A | 8/1997 | Hinchliffe et al. | |
| 5,697,915 A | 12/1997 | Lynn | |
| 5,738,144 A | 4/1998 | Rogers | |
| 5,749,861 A | 5/1998 | Guala et al. | |
| 5,806,831 A | 9/1998 | Paradis | |
| 5,817,069 A | 10/1998 | Arnett | |
| 5,833,674 A | 11/1998 | Turnbull et al. | |
| 5,954,698 A | 9/1999 | Pike | |
| 5,967,490 A | 10/1999 | Pike | |
| 6,039,302 A | 3/2000 | Cote, Sr. et al. | |
| 6,077,244 A | 6/2000 | Botich et al. | |
| 6,117,108 A | 9/2000 | Woehr et al. | |
| 6,171,287 B1 | 1/2001 | Lynn et al. | |
| 6,273,869 B1 | 8/2001 | Vaillancourt | |
| 6,287,280 B1 | 9/2001 | Lampropoulos et al. | |
| 6,485,473 B1 | 11/2002 | Lynn | |
| 6,575,960 B2 | 6/2003 | Becker et al. | |
| 6,595,981 B2 | 7/2003 | Huet | |
| 6,699,221 B2 | 3/2004 | Vaillancourt | |
| 6,719,726 B2 | 4/2004 | Meng et al. | |
| 6,740,063 B2 | 5/2004 | Lynn | |
| 6,883,778 B1 | 4/2005 | Newton et al. | |
| 7,008,404 B2 | 3/2006 | Nakajima | |
| 7,347,839 B2 | 3/2008 | Hiejima | |
| 7,396,346 B2 | 7/2008 | Nakajima | |
| 7,470,254 B2 | 12/2008 | Basta et al. | |
| 7,736,339 B2 | 6/2010 | Woehr et al. | |
| 7,914,494 B2 | 3/2011 | Hiejima | |
| 2006/0163515 A1 | 7/2006 | Ruschke | |
| 2007/0083157 A1 | 4/2007 | Belley et al. | |
| 2007/0083162 A1 | 4/2007 | O'Reagan et al. | |
| 2007/0233007 A1 | 10/2007 | Adams | |
| 2008/0039796 A1 | 2/2008 | Nakajima | |
| 2008/0108944 A1 | 5/2008 | Woehr et al. | |
| 2008/0287921 A1 | 11/2008 | Bennett | |
| 2009/0287154 A1 | 11/2009 | Harding et al. | |
| 2010/0204648 A1 | 8/2010 | Stout et al. | |
| 2010/0204675 A1 | 8/2010 | Woehr et al. | |
| 2010/0222746 A1 | 9/2010 | Burkholz | |
| 2011/0046570 A1* | 2/2011 | Stout | A61M 25/00 604/246 |
| 2011/0160662 A1 | 6/2011 | Stout et al. | |
| 2011/0160663 A1 | 6/2011 | Stout et al. | |
| 2012/0232498 A1* | 9/2012 | Ma | A61M 25/0606 604/256 |
| 2013/0090607 A1 | 4/2013 | McKinnon et al. | |
| 2013/0090609 A1* | 4/2013 | Sonderegger | A61M 39/22 604/256 |
| 2013/0165867 A1 | 6/2013 | Isaacson et al. | |
| 2014/0276434 A1* | 9/2014 | Woehr | A61M 25/0075 604/164.08 |

FOREIGN PATENT DOCUMENTS

| | | |
|---|---|---|
| EP | 0 369 314 A2 | 5/1990 |
| EP | 0 440 426 A1 | 8/1991 |
| EP | 0 968 736 A1 | 1/2000 |
| EP | 1 129 740 A2 | 9/2001 |
| EP | 1 197 242 A1 | 4/2002 |
| EP | 1 679 043 A2 | 7/2006 |
| WO | 93/11696 | 6/1993 |
| WO | 96/41649 | 12/1996 |
| WO | 98/00195 | 1/1998 |
| WO | 99/34849 | 7/1999 |
| WO | 99/38562 | 8/1999 |
| WO | 2006/037638 A1 | 4/2006 |
| WO | 2006/059540 A1 | 6/2006 |
| WO | 2007/044878 A2 | 4/2007 |
| WO | 2008/014436 A2 | 1/2008 |
| WO | 2008/052790 A2 | 5/2008 |
| WO | 2009/114833 A1 | 9/2009 |
| WO | 2010/093791 A1 | 8/2010 |
| WO | 2012/002015 A1 | 1/2012 |

* cited by examiner

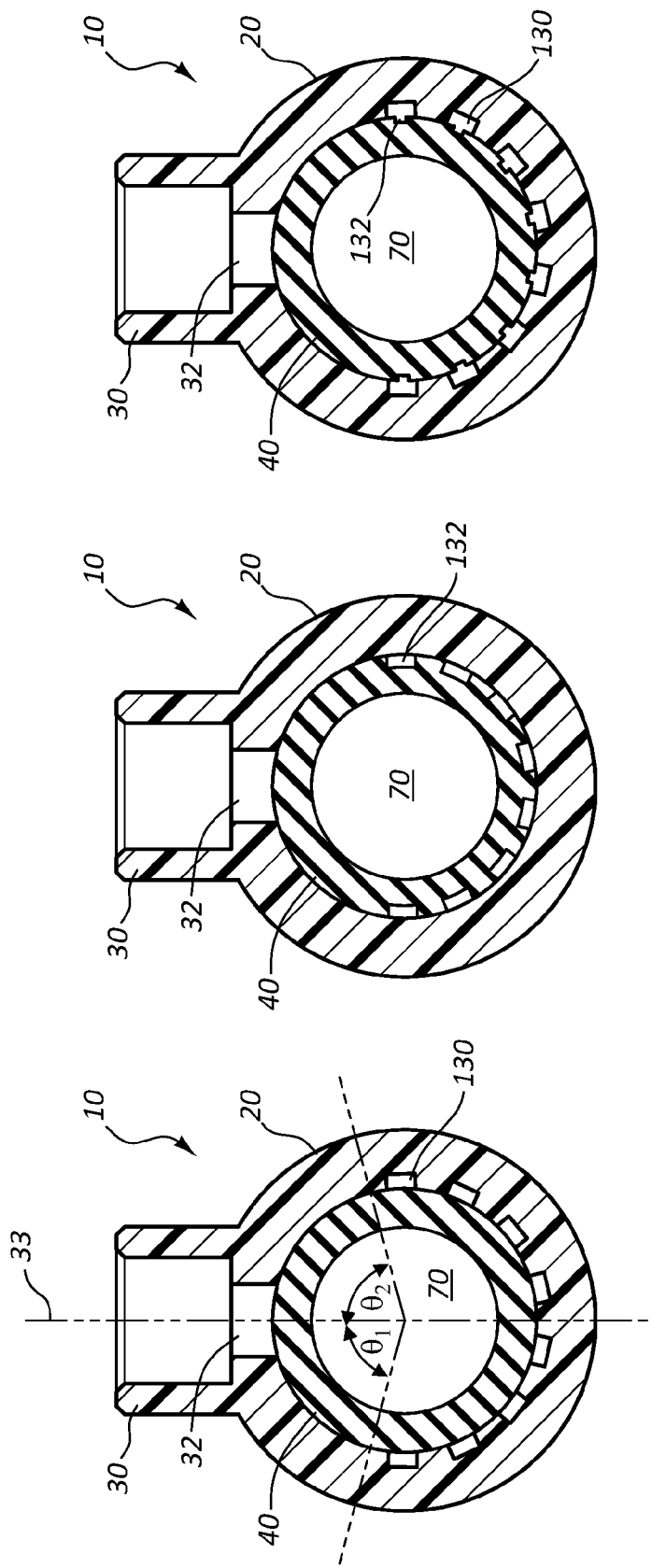

PORTED CATHETER ADAPTER HAVING COMBINED PORT AND BLOOD CONTROL VALVE WITH VENTING

RELATED APPLICATIONS

This application claims priority to U.S. Provisional Patent Application Ser. No. 61/929,708, filed Jan. 21, 2014, and entitled PORTED CATHETER ADAPTER HAVING COMBINED PORT AND BLOOD CONTROL VALVE WITH VENTING, which is incorporated herein in its entirety.

BACKGROUND

Intravenous infusion systems are commonly used to access the vasculature of a patient as part of an infusion therapy procedure. An intravenous infusion system generally includes a fluid reservoir of IV bag that is connected to the patient via an intravenous catheter. The catheter is commonly coupled to a catheter adapter having a Luer-lock connector, or other connector-type for coupling the catheter adapter to a syringe, a section of intravenous tubing, or some other external Luer device. Fluid from the IV bag flow into the patient via the catheter adapter and the intravenous catheter.

In some instances, the catheter adapter further includes a blood control valve that is positioned within a fluid pathway running though the catheter adapter. The blood control valve divides the fluid pathway or lumen into proximal and distal chambers, and allows selective flow of fluid through the fluid pathway. For example, the blood control valve may include a slit that may be bypassed when an external Luer device is coupled to the catheter adapter and directly engaging the valve. Upon removing the external Luer device, the slit is closed to prevent blood from leaking out of the catheter adapter.

A catheter adapter may further include a valve actuator that is contacted by an external or secondary infusion device, such as a Luer device, and advanced through the slit of the valve. The valve actuator is generally advanced through the valve to provide a temporary pathway through the valve. Upon removal of the secondary infusion device, the resilient nature of the valve backs the valve actuator out of the valve slit.

In some instances, the catheter adapter further comprises a side port whereby to inject a fluid directly into the inner lumen of the catheter adapter while the catheter adapter is coupled to a separate infusion device, such as a section of intravenous tubing. The catheter adapter further comprises a port valve that is positioned to form a fluid-tight seal with a pathway of the side port to prevent fluids within the lumen of the catheter adapter from leaking out of the side port. When a fluid is injected through the side port, the port valve is temporarily deformed by the fluid pressure of the injected fluid, thereby providing a gap through which the injected fluid is permitted to flow into the lumen of the catheter adapter. Following the injection, the port valve is restored to its original conformation, there again forming a fluid-tight seal.

Thus, while systems and methods currently exist to simultaneously control blood flow and allow a fluid to be injected via a side port, challenges still remain. Accordingly, it would be an improvement in the art to augment or replace current techniques with the system and methods discussed herein.

BRIEF SUMMARY OF THE INVENTION

The present invention has been developed in response to problems and needs in the art that have not yet been fully resolved by currently available systems and methods. Thus, these systems and methods are developed to provide a ported catheter adapter having a combined port and blood control valve with venting. Thus, the systems and methods of the present invention provide an infusion device having a single valve that control fluid and air flow through the lumen of the ported catheter adapter. The present invention further comprises a valve actuator having various features for retaining the valve actuator within the lumen of the ported catheter adapter and preventing over-insertion of the valve actuator through the membrane of the valve.

In some implementations, a ported catheter assembly is provided comprising a catheter adapter having a proximal end, a distal end and a lumen extending therebetween, the catheter adapter further comprising a side port forming a pathway through a sidewall of the catheter adapter and in communication with the lumen. The catheter assembly further comprises a combined port and blood control valve disposed within the lumen and dividing the lumen into a proximal chamber and a distal chamber. The valve comprises a body having a surface that forms a fluid-tight, defeatable seal with the pathway of the side port. When a fluid is injected into the side port, the body of the valve is temporarily deformed, thereby providing a gap between the outer surface of the valve and the inner surface of the ported catheter adapter. The fluid from the side port flows through this gap and into the proximal chamber of the ported catheter adapter. Following the injection, the body of the valve resumes its initial conformation, thereby reestablishing the fluid-tight seal against the pathway of the side port.

In some instances, the device further includes a valve actuator having an outer diameter and disposed within the proximal chamber and having a base, a tip and a body extending therebetween. The tip is positioned proximate to the membrane of the valve and the base is positioned proximate to the proximal end of the catheter adapter. The catheter assembly further comprises an actuator retention tab having an outer diameter and being positioned on an outer surface of the valve actuator body.

The valve generally comprises a flexible tube having an outer diameter that is approximately the same size as an inner diameter of the lumen, whereby the valve is retained within the lumen by an interference fit. The proximal end of the catheter adapter further comprises and opening through which a separate device may be inserted to contact the base of the valve actuator and advance the tip of the valve actuator through a slit in the membrane of the valve. In some instances, the valve actuator comprises a plurality of windows or vents that are provided to permit fluid to flow in and out of an inner lumen of the valve actuator.

The valve further comprises a plurality of vents forming horizontal channels on the outer surface of the valve. These vents comprise cross-section areas that are selected to permit the passage of air while preventing passage of fluids. The vents are positioned on the outer surface of the valve so as to prevent the vents from overlapping the pathway of the side port. Thus, fluid that is injected into the inner lumen of the ported catheter adapter is prevented from entering the vents, and air within the vents is prevented from exiting the ported catheter adapter via the pathway and the side port.

In some instances, truncated vents are provided having distal openings in fluid communication with the distal chamber, and proximal ends that are in fluid communication with a vent ring. The vent ring forms a semi-annular channel in the outer surface of the valve and comprises one or more venting holes providing a pathway through the sidewall of the valve. Thus, air within the distal chamber passes into the proximal chamber by flowing through the truncated vents, into the vent ring and through the venting hole.

In some instances, an annular vent ring is provided and used in combination with truncated vents that are positioned around the entire circumference of the valve. For these embodiments, the annular vent ring is positioned such that is does not overlap the pathway of the side port. In some implementations, a distance is provided between the pathway of the side port and the annular vent ring, wherein this distance insures that the proximal body portion of the valve may deform to allow passage of fluid being injected through the side port, without allowing fluid communication between the annular vent ring and the pathway of the side port.

The present invention further includes various embodiments comprising one or more vents formed in the inner surface of the ported catheter adapter and interposed between the outer surface of the valve and the catheter adapter, wherein the one or more vents provide a function similar to those discussed in connection with the vents provided on the outer surface of the valve.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

FIG. 3, shown in parts A-C, shows various cross-section end views of a ported catheter adapter having a plurality of vents in accordance with various representative embodiments of the present invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1:
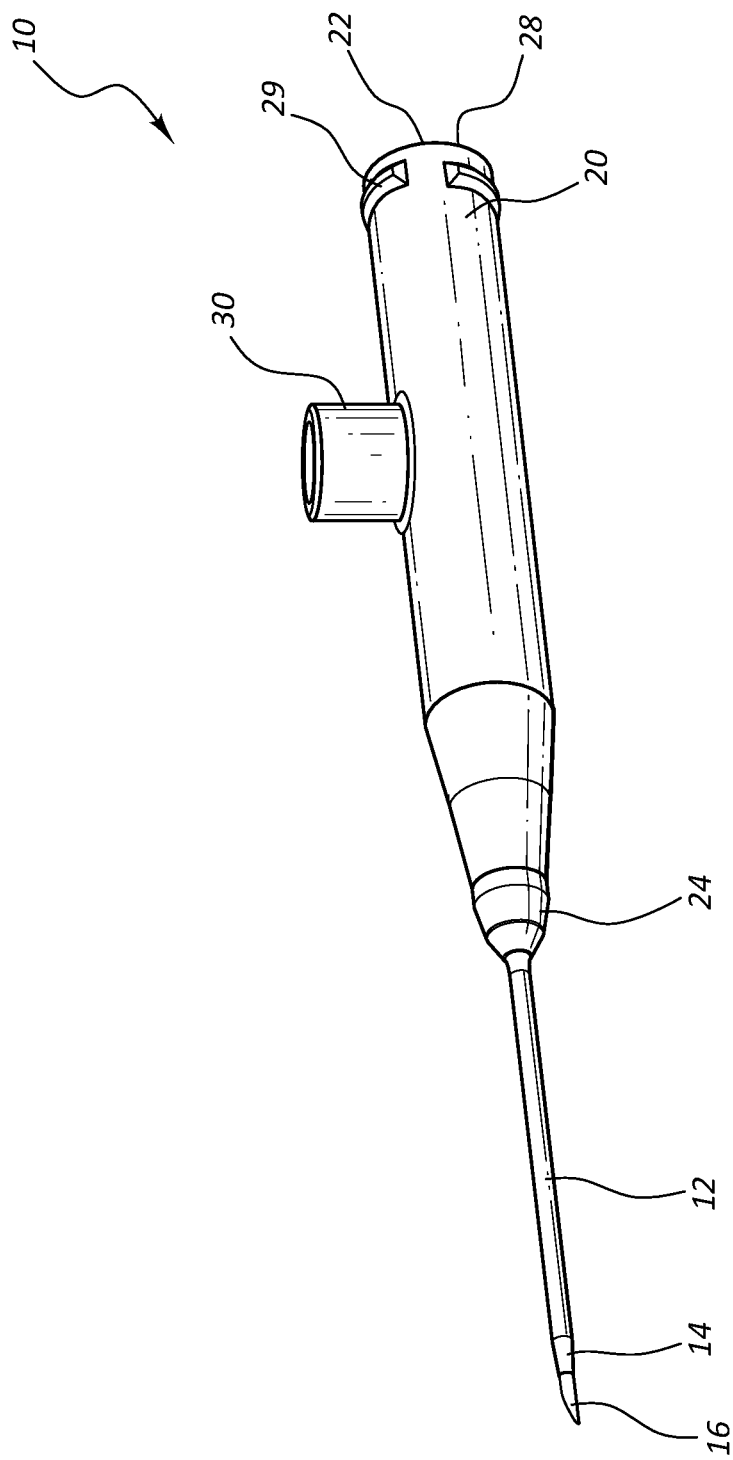
FIG. 1 is a perspective view of a ported infusion therapy device in accordance with a representative embodiment of the present invention.

Referring now to FIG. 1, a ported infusion therapy device 10 is shown. Device 10 generally comprises various features and elements to enable subcutaneous or intravenous infusion of a fluid or medicament into a patient. In some instances, device 10 further comprises feature to enable removal of a fluid from a patient, such as blood.

Device 10 generally comprises a ported catheter adapter 20 having a proximal end 22, a distal end 24 and a lumen 26 extending therebetween. In some instances, catheter adapter 20 further comprises a side port 30 forming a pathway through a sidewall of catheter adapter 20 and in communication with lumen 26. A valve 40 (shown in FIGS. 2-7) is placed within lumen 26 so as to provide a defeatable barrier to control the flow of fluids through lumen 26. In some instances, valve 40 comprises a membrane that divides lumen 26 into a proximal chamber and a distal chamber, as discussed in detail, below. In some instances, the membrane comprises a slit that may be opened by inserting a device through the slit, such as a valve actuator. In other instances, the slit may be temporarily biased into an opened position by inserting a fluid into proximal end 22 of adapter 20. Upon removal of the valve actuator from the slit, or as the fluid pressure decreases within lumen 26, the resilient nature of the membrane causes the slit to close, thereby once again preventing passage of fluid through lumen 26.

Valve 40 further comprises a tubular body that provides a barrier between side port 30 and lumen 26. Valve 40 generally comprises a resilient, flexible material that is easily deformed when fluid is introduced to port 30 via a syringe or other compatible device. For example, in some instances valve 40 comprises silicone, polytetrafluoroethylene, or a similar polymer material. Upon deformation of valve 40, fluid from the syringe is permitted to bypass the deformed valve and flow into lumen 26. As the fluid pressure decreases, the resilient nature of the valve's material causes valve 40 to restore its original shape, thereby once again blocking the fluid pathway.

Device 10 further comprises a catheter 12 that is coupled to distal end 24 and which is configured for insertion into a patient. In some instances, catheter 12 comprises a rigid plastic or metallic material having a sharpened distal end that can pierce the patient's skin and gain access to the vasculature or subcutaneous tissues of the patient. In other instance, catheter 12 comprises a flexible material having an inner diameter through which an introducer needle 16 is inserted. Introducer needle 16 comprises a rigid metallic material having a sharpened distal end that extends through catheter 12 and is exposed beyond the tip 14 of catheter 12. The introducer needle is capable of piercing the skin to provide access to the vasculature or subcutaneous tissues of the patient. Once access is obtained, tip 14 of catheter 12 is inserted through the newly formed opening and into the desired location within the patient. Introducer needle 16 is then withdrawn from device 10, and catheter 12 is left disposed within the patient.

Proximal end 22 further comprises an opening 28 for receiving a secondary infusion therapy device 50, such as a syringe or intravenous fluid line. In some instances, proximal end 22 comprises a set of threads 29 configured to threadedly receive the secondary device 50 in a secure manner. Opening 28 may further comprise a tapered opening whereby to receive secondary device 50 via an interference or friction fit. Proximal end 22 and opening 28 may alternatively comprises various surfaces and other features to enable coupling to a needle hub, a diagnostic device, and other suitable infusion therapy equipment.

Figure 2A:
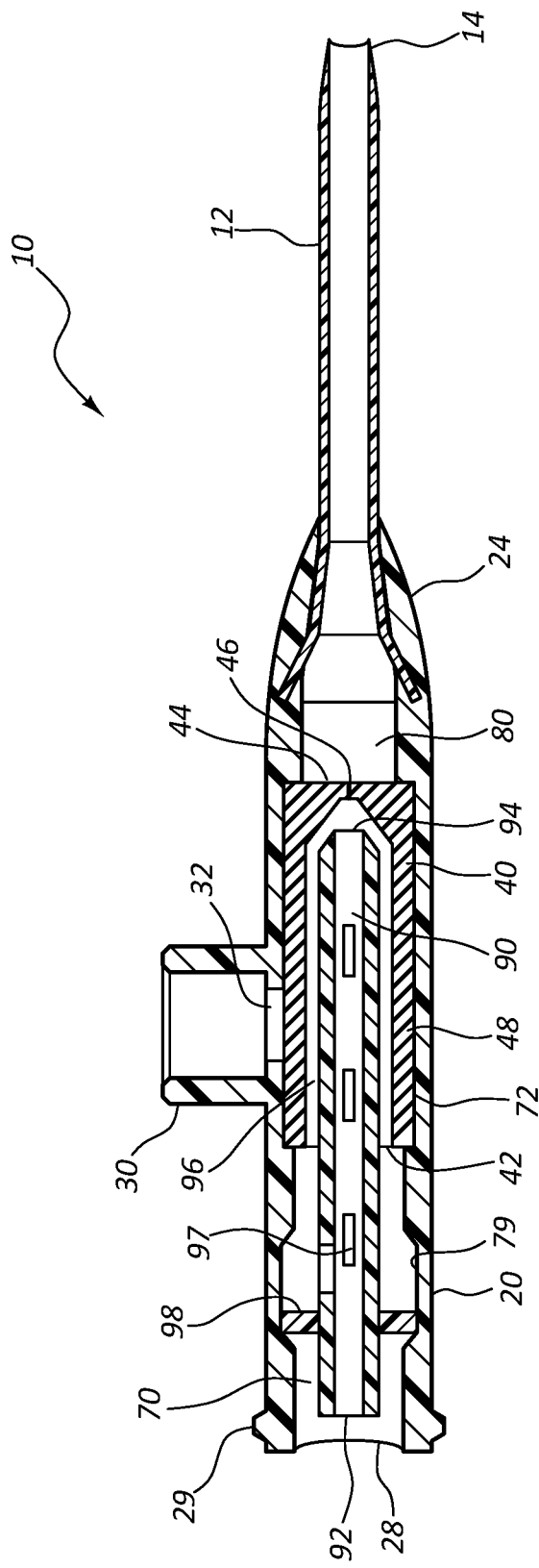
FIG. 2A is a cross-section, side view of a ported catheter adapter having a combined port and blood control valve, a valve actuator, and an actuator retention tab, and being shown prior to activation in accordance with a representative embodiment of the present invention.

Referring now to FIG. 2A, a cross-section side view catheter adapter 20 is shown in an inactivated state. Catheter adapter 20 further comprises a blood control valve 40 that is disposed within lumen 26, thereby dividing lumen 26 into proximal 70 and distal 80 fluid chambers. In some instances, the inner surface of adapter 20 comprises an annular recess or groove 72 having a length that is approximately equal to the length of blood control valve 40. The inner diameter of groove 72 is approximately equal to the outer diameter of valve 40. Valve 40 is thus fitted or seated into groove 72 to provide an assembled device. Generally, valve 40 is seated into groove 72 in a secure manner to prevent unintended passage of liquids between the outer surface of valve 40 and the inner surface of adapter 20 or groove 72. In some instances, the inner diameter of groove 72 is slightly smaller than the outer diameter of valve 40, thereby providing an interference fit of valve 40 within groove 72. In other instances, valve 40 is retained within groove 72 via an adhesive or an epoxy material.

Valve 40 may comprise any shape or structure that is compatible with the teachings of the instant invention. In some instances, valve 40 comprises a cylindrical structure having a proximal opening 42, a distal membrane 44 comprising a slit 46, and a body 48 extending therebetween. Slit 46 comprises a sealed interface which provides a fluid-tight seal, thereby preventing fluid from bypassing valve 40.

Valve 40 comprises a flexible, resilient material that may be selectively deformed to open slit 46 to permit passage of fluids. For example, in some embodiments increased fluid pressure within proximal fluid chamber 70 will result in valve 40 being temporarily deformed, thereby permitting fluid within proximal chamber 70 to bypass valve 40 through slit 46 and flow into distal fluid chamber 80 of lumen 26. In other instances, slit 46 is biased into an opened position by temporarily or permanently inserting an object through slit 46, such as a valve actuator 90.

Figure 2B:
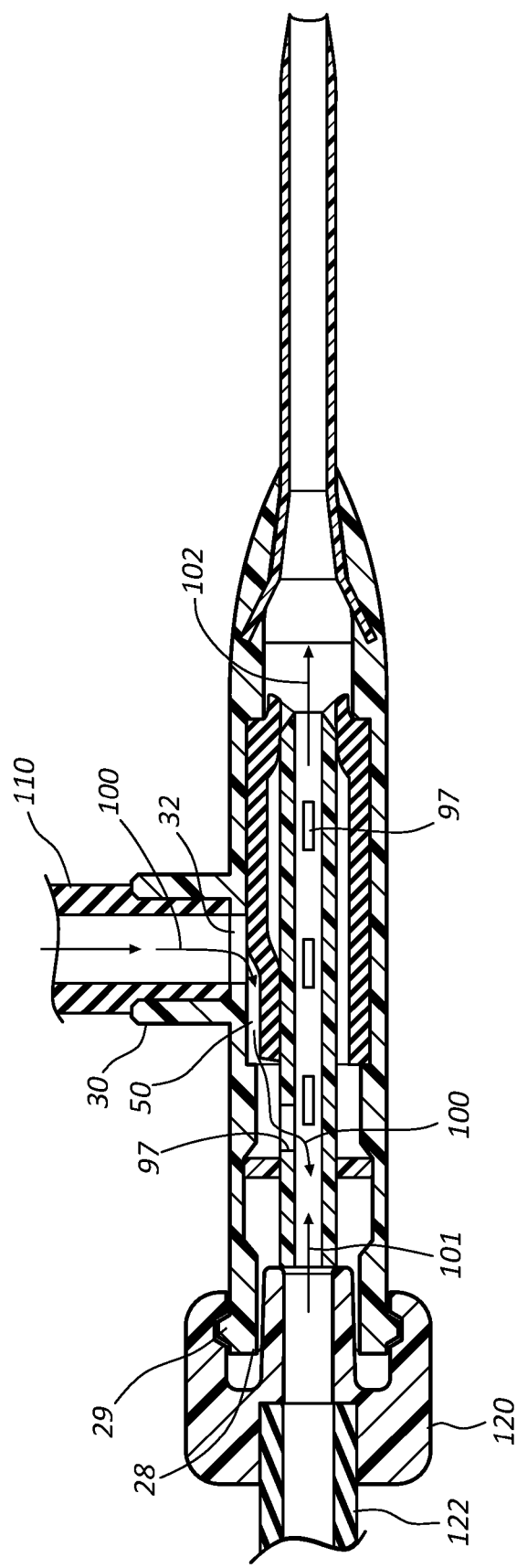
FIG. 2B is a cross-section, side view of a ported catheter adapter having a combined port and blood control valve, a valve actuator, and an actuator retention tab, and being shown following activation and a fluid being injected via the side port in accordance with a representative embodiment of the present invention.

Body 48 of valve 40 is positioned within lumen 26 so as to provide a fluid-tight, defeatable barrier between proximal chamber 70 and pathway 32 of side port 30. Upon injecting a fluid 100 from a secondary infusion device 110 into side port 30 and through pathway 32, body 48 is temporarily deformed to provide a gap 50 between groove 72 and the outer surface of valve 40. Fluid 100 is thus permitted to flow through gap 50 and into proximal chamber, as shown in FIG. 2B. Upon removal of secondary infusion device 110 from side port 30, the resilient nature of valve 40 causes body 48 to resume its original conformation, thereby once again establishing a fluid-tight seal between body 72 and pathway 32, and preventing subsequent flow of fluids through pathway 32, as shown in FIGS. 2A and 2C.

Referring again to FIG. 2A, device 10 further comprises a valve actuator 90 that is disposed within proximal chamber 70. Valve actuator 90 may comprise any shape, structure or configuration that is compatible with any of the various representative embodiments or teachings of the invention described herein. In some instances, valve actuator comprises a base 92, a tip 94, and a body 96 extending therebetween. Valve actuator 90 further comprises a hollow interior through which a fluid 100 may pass. In some instances, body 96 comprises one or more fluid vents or windows 97 forming a fluid pathway through a sidewall of the valve actuator 90 and in communication with lumen 26, thereby providing diverse flow patterns for a fluid passing through lumen 26 and valve actuator 90. Thus, a fluid within the hollow interior of valve actuator 90 may pass through the one or more windows 97 and into lumen 26.

Base 92 is generally positioned proximate to opening 28 of catheter adapter 20, thereby being accessible to a secondary infusion therapy device 120, such as a male Luer connector coupled to a section of intravenous tubing 122. Tip 94 is positioned proximate to membrane 44 and slit 46. Tip 94 is advanced through slit 46 as base 92 is pushed in distal direction 100 as secondary infusion therapy device 120 is inserted through opening 28 and threadedly secured to proximal end 22, as shown in FIGS. 2B and 2C. Upon removal of secondary device 120, the resilient nature of valve 40 causes membrane 44 to restore its original formation, thereby backing tip 94 out of slit 46, and sliding valve actuator 90 in proximal direction 102, thereby restoring the fluid-tight seal of slit 46, as shown in FIG. 2A.

Figure 2C:
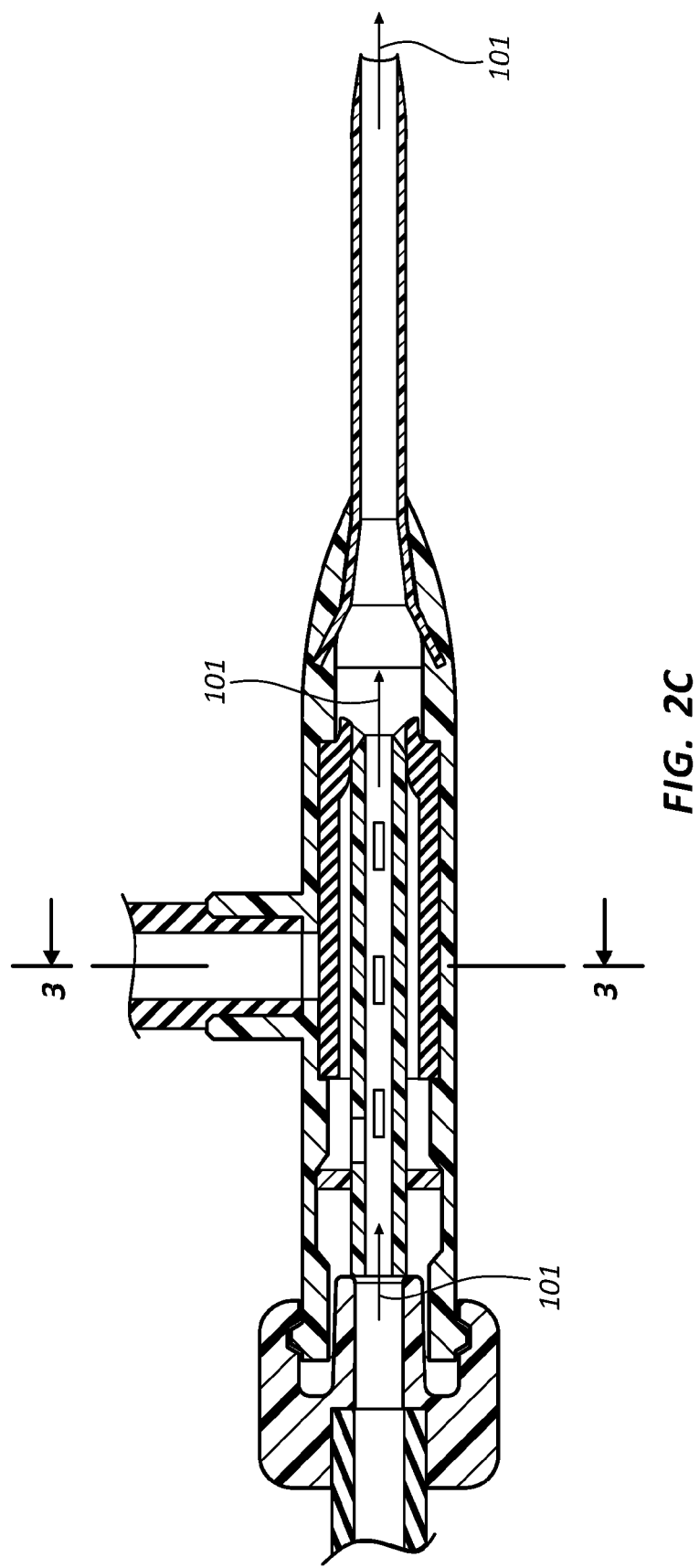
FIG. 2C is a cross-section, side view of a ported catheter adapter having a combined port and blood control valve, a valve actuator, and an actuator retention tab, and being shown following activation and a fluid being infused via the proximal opening in accordance with a representative embodiment of the present invention.

With continued reference to FIGS. 2A-2C, valve actuator 90 may further comprise an actuator retention tab 98. Retention tab 98 generally comprises an annular protrusion or other feature on the outer surface of valve actuator 90 that interacts with a proximal groove 79 formed on the inner surface of adapter 20 at a position between proximal opening 42 of valve 40 and proximal opening 28 of adapter 20. The interaction between retention tab 98 and proximal groove 79 limits the proximal and distal movement of valve actuator 90 within lumen 26. In some instances, retention tab 98 comprises an outer diameter that is greater than the outer diameter of body 96 and less than an inner diameter of proximal groove 79, thereby permitting retention tab 98 to slide freely within proximal groove 79. The maximum distance that valve actuator 90 is permitted to travel within lumen 26 (in proximal and distal directions) is thus limited by the width of proximal groove 79.

In some embodiments, the width and placement of proximal groove 79 is selected such that base 92 is prevented from exiting proximal opening 28 of adapter 20. The width and placement of proximal groove 79 is further selected to ensure tip 94 is advanced through slit 46 to a desired depth. For example, in some instances it may be desirable to prevent over-insertion of tip 94 through slit 46. Over-insertion may be understood to describe a penetration depth of tip 94 into slit 46 where valve 40 is incapable of backing tip 94 out of slit 46 when secondary infusion device 120 is removed from opening 28. Over-insertion of tip 94 into slit 46 may thus prevent slit 46 from reforming a fluid-tight seal. Accordingly, in some embodiments, the width of proximal groove 79 is selected so that the maximum permitted distal movement of retention clip 98 prevents tip 94 from being over-inserted in slit 46.

Similarly, the width and placement of proximal groove 79 may be selected to ensure that tip 94 of valve actuator 90 is permitted to penetrate slit 16 to a minimum insertion depth. Minimum insertion depth may be understood to describe a penetration depth where the surface area of the opening provided in slit 46 is greater than or equal to the surface area of the opening of tip 94. As such, the minimum insertion depth through slit 46 provides an opening or fluid pathway through valve 40 that does not impede or interfere with the flow of fluid passing through valve actuator 90. Thus, the width and position of proximal groove 79, as well as the distance between retention ring 98 and tip 94 may be selected to ensure proper insertion depth of tip 94 through slit 46.

Prior to activation, tip 94 of valve actuator 90 is positioned adjacent membrane 44, and base 92 is positioned adjacent opening 28 of adapter 20, as shown in FIG. 2A. Further, retention tab 98 is positioned in a maximum, proximal location within proximal groove 79. Upon insertion of secondary infusion device 120 into opening 28, base 92 is contacted by device 120 and valve actuator 90 is advanced in a distal direction, thereby moving retention tab 98 to a maximum distal position within proximal groove 79, as shown in FIGS. 2B and 2C. Tip 94 is thus advanced into membrane 44 and partially inserted through slit 46. In some instances, tip 94 is over-inserted through slit 46, thereby providing a permanent pathway through membrane 44.

With reference to FIG. 2B, in some instances fluid 100 is introduced into lumen 26 via pathway 32 of side port 30 from secondary infusion device 110. The injected fluid 100 biases body 48 against valve actuator 90, thereby providing gap 50 through which fluid 100 flows. Accordingly, in some embodiments the outer diameter of valve actuator 90 is slightly less than an inner diameter of valve 40, thus allowing valve 40 to be temporarily deformed.

In some preferred embodiments, fluid 100 bypasses valve 40 and enters proximal chamber 70 of lumen 26. Fluid 100 is then intermixed with fluid 101 from secondary infusion device 120. The mixed fluids 102 then flow though valve actuator 90, out of valve 40, and into catheter 12 as part of an infusion therapy. Upon removal of secondary infusion device 110, body 48 returns to its original shape, thereby preventing fluid from exiting lumen 26 via gap 50 and pathway 32 of side port 30, as shown in FIG. 2C. When the infusion therapy is complete, secondary infusion device 120 is removed from proximal end 22, whereupon tip 94 of valve actuator 90 is backed out of membrane 44 as slit 46 returns to its original, closed position, thereby preventing fluids from flowing between proximal and distal chambers 70 and 80, as shown in FIG. 2A.

Some embodiments of the present invention further comprise a vent 130 interposed between the outer surface of the valve 40 and an inner surface of the lumen 70 of the catheter adapter 20, as shown in FIGS. 3A-9. Vent 130 generally comprises a groove or recess having a cross-section area that is selected to permit passage of air while preventing the passage of fluid. For example, during catheterization it is desirable to minimize pressure buildup in distal chamber 80 due to blood entering the chamber. Increased pressure in distal chamber 80 may prevent blood from flowing through catheter 12 to provide flashback and indicate proper venous insertion. Accordingly, vents 130 permit air pressure within distal chamber 80 to be transferred to proximal chamber 70, thereby providing equalized pressures within the adjacent chambers.

It is also desirable to prevent blood and other fluids from bypassing membrane 44 through vents 130, thereby preventing undesirable exposure to fluids that may exit proximal opening 28 of catheter adapter 20. Accordingly, in some instances the cross-section area of vents 130 is selected to permit passage of air while preventing passage of fluids. For example, in some instances the cross-section area of vent 130 is selected such that the surface tension of the fluid prevents the fluid from entering into, and passing through vents 130.

In some instances, vents 130 comprise horizontal channels that are formed in the inner surface of catheter adapter 20, as shown in FIG. 3A. Vents 130 generally comprise a length that is greater than or equal to the length of valve 40, whereby air is permitted to bypass valve 40. In other instances, vents 132 comprise horizontal channels that are formed in the outer surface of valve 40, as shown in FIG. 3B. Further, in some instances a vent is provided comprising a horizontal channel 130 formed in the inner surface of catheter adapter 20 combined with a horizontal channel 132 formed on the outer surface of valve 40, wherein the combined cross-sectional areas of the two channels prevents passage of a fluid, as shown in FIG. 3C. In one embodiment, horizontal channel 132 comprises a cross-sectional area that is less than a cross-sectional area of horizontal channel 130.

Vents 130 are generally located at positions that do not overlap with pathway 32 of side port 30. With reference to FIG. 3A, vent 130 is shown radially spaced from a central axis 33 of pathway 32 by angle θ, which angle is comprised of $\theta_1$ and $\theta_2$. In some instances, angle θ is approximately 120°. In other instances, angle θ is from approximately 30° to approximately 180°. Further, in some instances angle θ is greater than 180°.

Angles $\theta_1$ and $\theta_2$ may be equal angles or may include non-equal angles. In all instances, angle θ is selected to prevent fluid communication between vents 130 and pathway 32. Accordingly, angle θ prevents a fluid that is injected into side port 30 and pathway 32 from flowing into vents 130. Conversely, angle θ is selected to prevent air within vent 130 from passing into pathway 32 and side port 30.

Figure 4A:
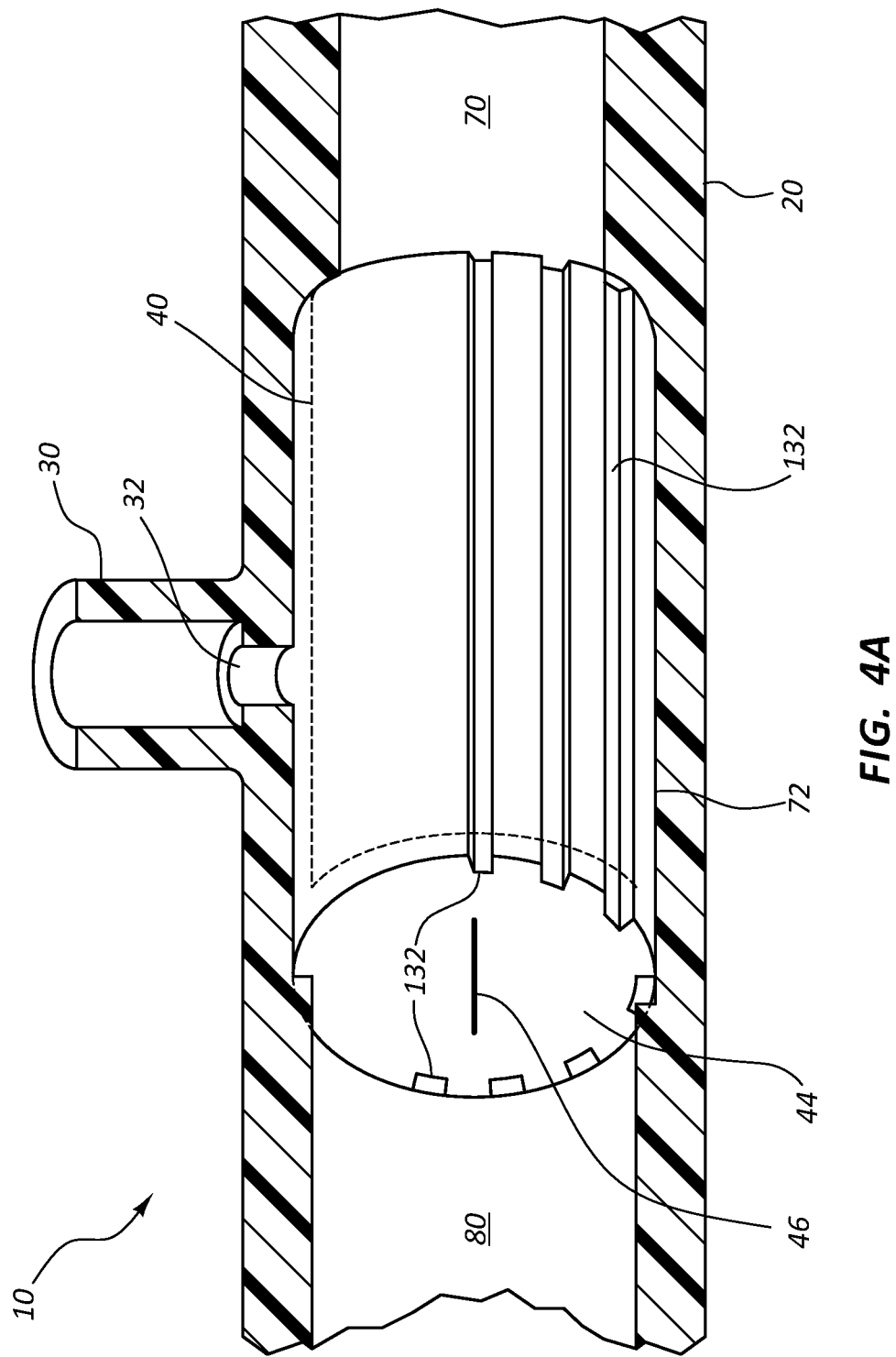
FIG. 4A shows a partial cross-section perspective side view of a ported catheter adapter having a vented valve comprising a plurality of horizontal vents in accordance with a representative embodiment of the present invention.

Referring now to FIG. 4A, a partial cross-section perspective side view of catheter adapter 20 and valve 40 is shown. In some instances, vents 132 comprise horizontal channels formed in the outer surface of valve 40 extending the entire length of valve 40. Vents 132 comprise a depth that is greater than the depth of annular groove 72, such that the proximal and distal openings of vents 132 are exposed to proximal and distal chambers 70 and 80, respectively. In some instances, the thickness of membrane 44 adds rigidity to the distal end of valve 40, thereby preventing membrane 44 from collapsing or deforming when a fluid is injected through side port 30 and pathway 32. Accordingly, the injected fluid deforms the proximal end of valve 40, thereby displacing the fluid into proximal chamber 70.

Figure 4B:
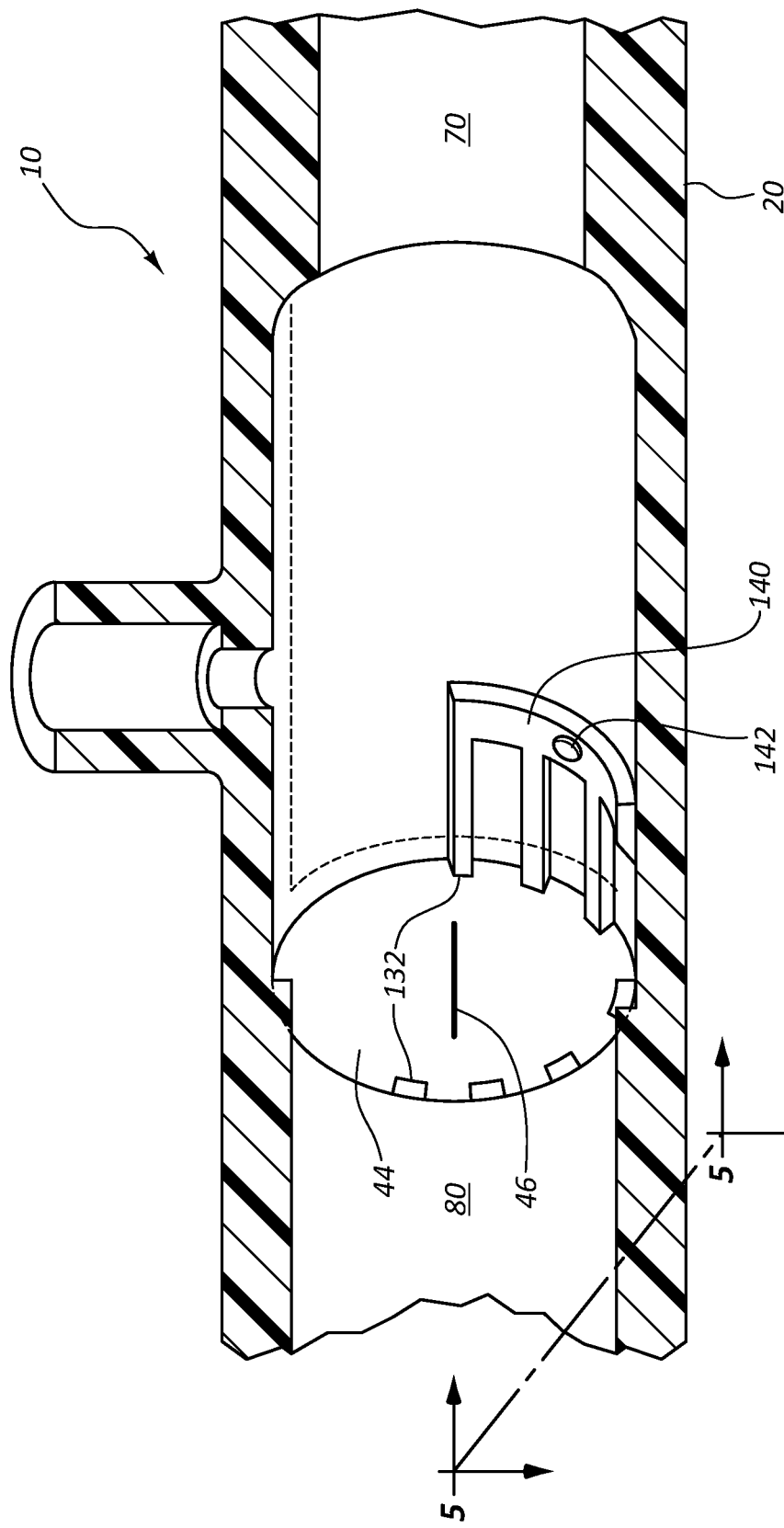
FIG. 4B shows a partial cross-section perspective side view of a ported catheter adapter having a vented valve comprising a plurality of horizontal vents, a vent ring and a venting hole in accordance with a representative embodiment of the present invention.

Referring now to FIG. 4B, a partial cross-section perspective side view of catheter adapter 20 and valve 40 is shown. In some instances valve 40 comprises a plurality of vents 132 having a distal opening in fluid communication with the distal fluid chamber 80, and further comprising a proximal opening in fluid communication with a vent ring 140. Vent ring 140 comprises a semi-annular recess formed in the outer surface of valve 40. In some instances, vent ring 140 forms a recessed channel that is perpendicular to vents 132. Vent ring 140 comprises a length that is equal to a radial distance between the topmost vents 132, or between the first and last horizontal vent channels. Vent ring 140 intersects each vent 132 thereby providing fluid communication between each of the individual vent channels.

Vent ring 140 further comprises one or more venting holes 142 that provide fluid communication between vents 132, vent ring 140, and proximal chamber 70. In some instances, venting hole 142 comprises a cross-section area that is equal to the sum of each of the cross-section areas of vents 132. As such, venting hole 142 permits uninterrupted air flow through vents 132. In some instances, vent ring 140 comprises a plurality of venting holes 142, wherein the sum of each of the cross-section areas of the venting holes is equal to, or greater than the sum of each of the cross-section areas of vents 132.

Figure 5:
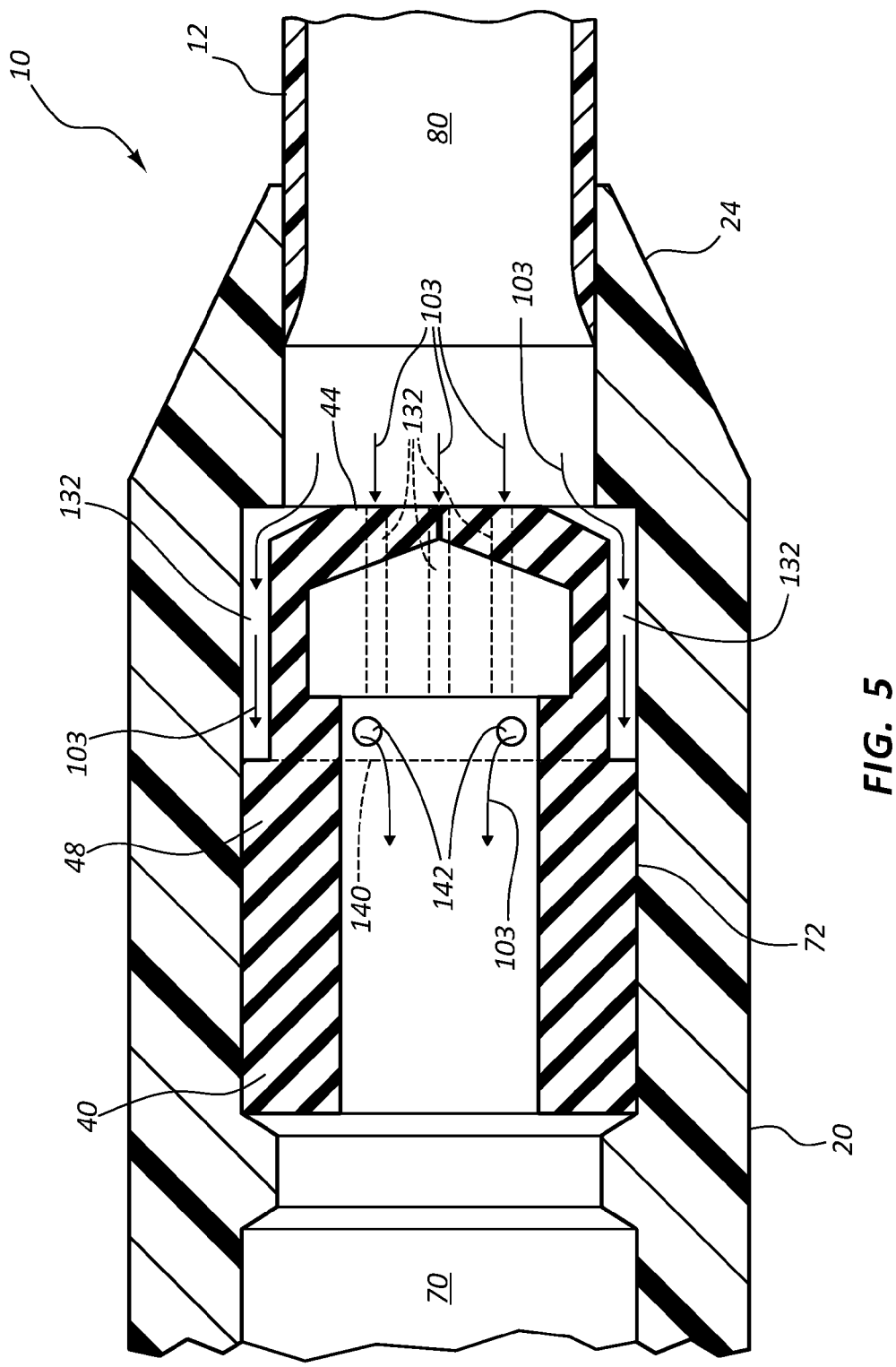
FIG. 5 shows a cross-section top view of a vented valve in a ported catheter adapter in accordance with a representative embodiment of the present invention.
Figure 6:
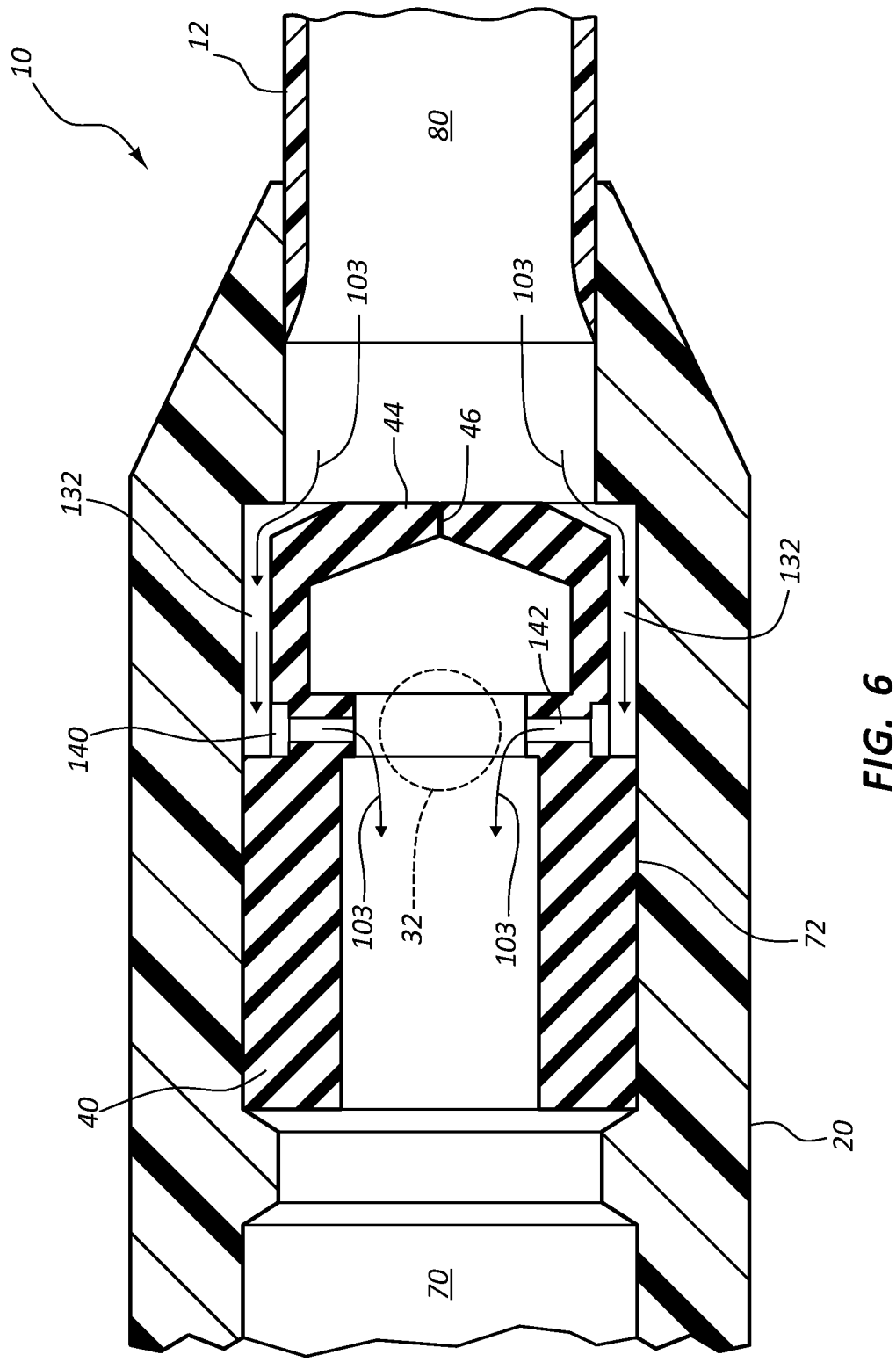
FIG. 6 shows a cross-section bottom view of the vented valve and ported catheter adapter of FIG. 5 in accordance with a representative embodiment of the present invention.

Referring now to FIG. 5, a cross-section top view of ported infusion therapy device 10 is shown. As shown, air 103 travels through vents 132 and into vent ring 140. Air 103 within vent ring 140 then passes through body 48 via venting holes 142 and into proximal chamber 70. Vents 132, vent ring 140 and venting holes 142 are positioned within the lumen of catheter adapter 20 such that these features do not overlap pathway 32, as shown in FIG. 6. Thus, air within vents 132, vent ring 140 and venting holes 142 do not pass into side port 30 or pathway 32.

In some instances, vent 40 comprises a thickened inner sidewall forming an inwardly projecting ring that correlates with vent ring 140, as shown in FIG. 6. In other instances, the thickened portion of the inner sidewall further correlates with or partially overlaps pathway 32, thereby adding further resistance to deformation of valve 40 at vent ring 140. In some instances, the thickened portion of the inner sidewall correlates only with vent ring 140, whereby the portion of the sidewall that correlates with or overlaps pathway 32 is of a standard thickness.

Figure 7:
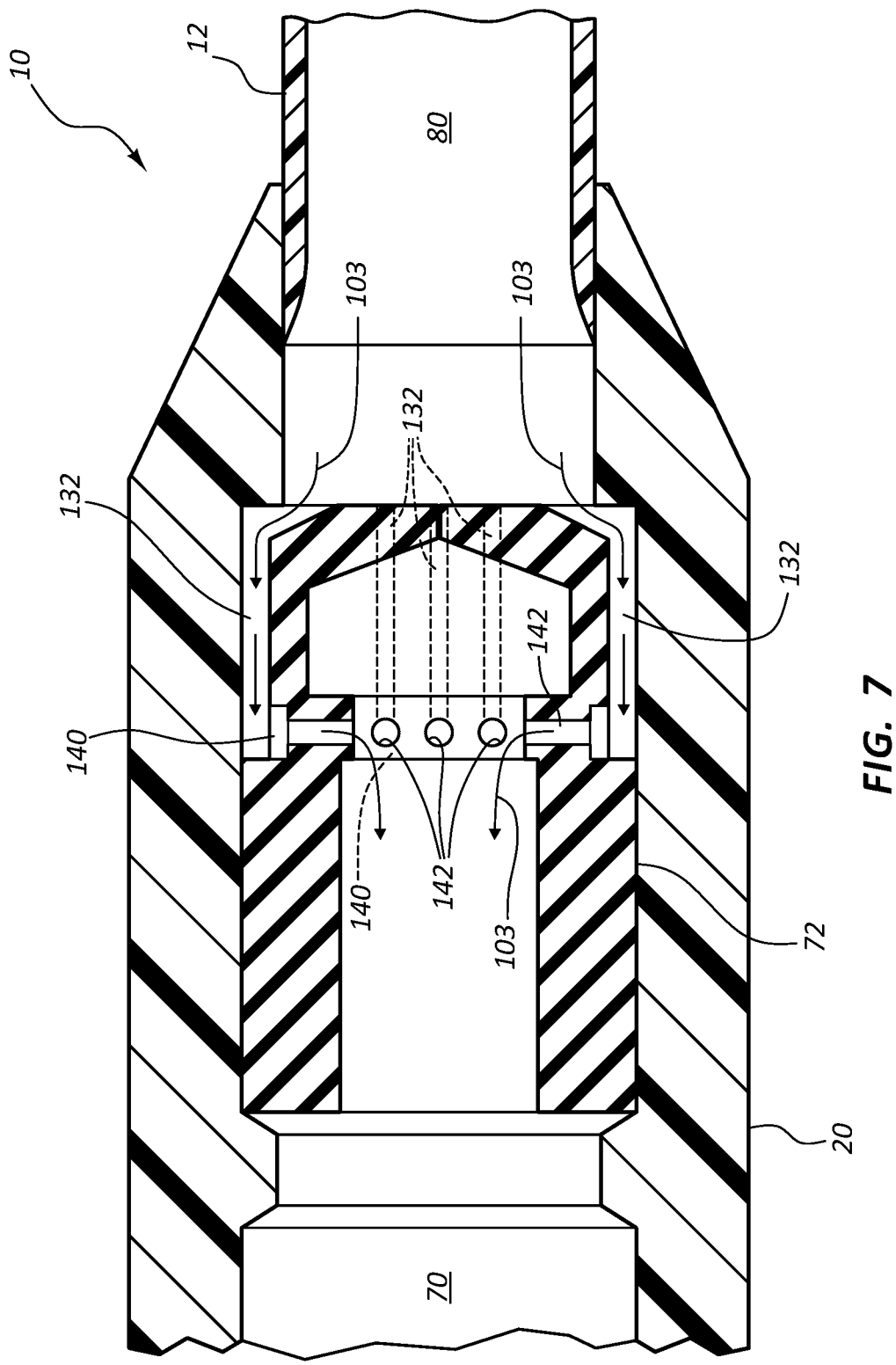
FIG. 7 shows a cross-section top view of a vented valve in a ported catheter adapter in accordance with a representative embodiment of the present invention.

Referring now to FIG. 7, a cross-section top view of ported infusion therapy device 10 is shown. In some instances, vent ring 140 comprises a plurality of venting holes 142, and a plurality of vents 132, wherein a separate venting hole 142 is provided for each vent 132. Venting holes 142 may comprise any cross-sectional area that achieved a desired rate of air flow through vents 132. In some instances, venting holes 142 comprise a cross-sectional area that is greater than the cross-section area of vents 132. In other instances, venting holes 142 comprise a cross-sectional area that is approximately equal to the cross-sectional areas of vents 132, as shown in FIGS. 8A and 8B.

Figure 8A:
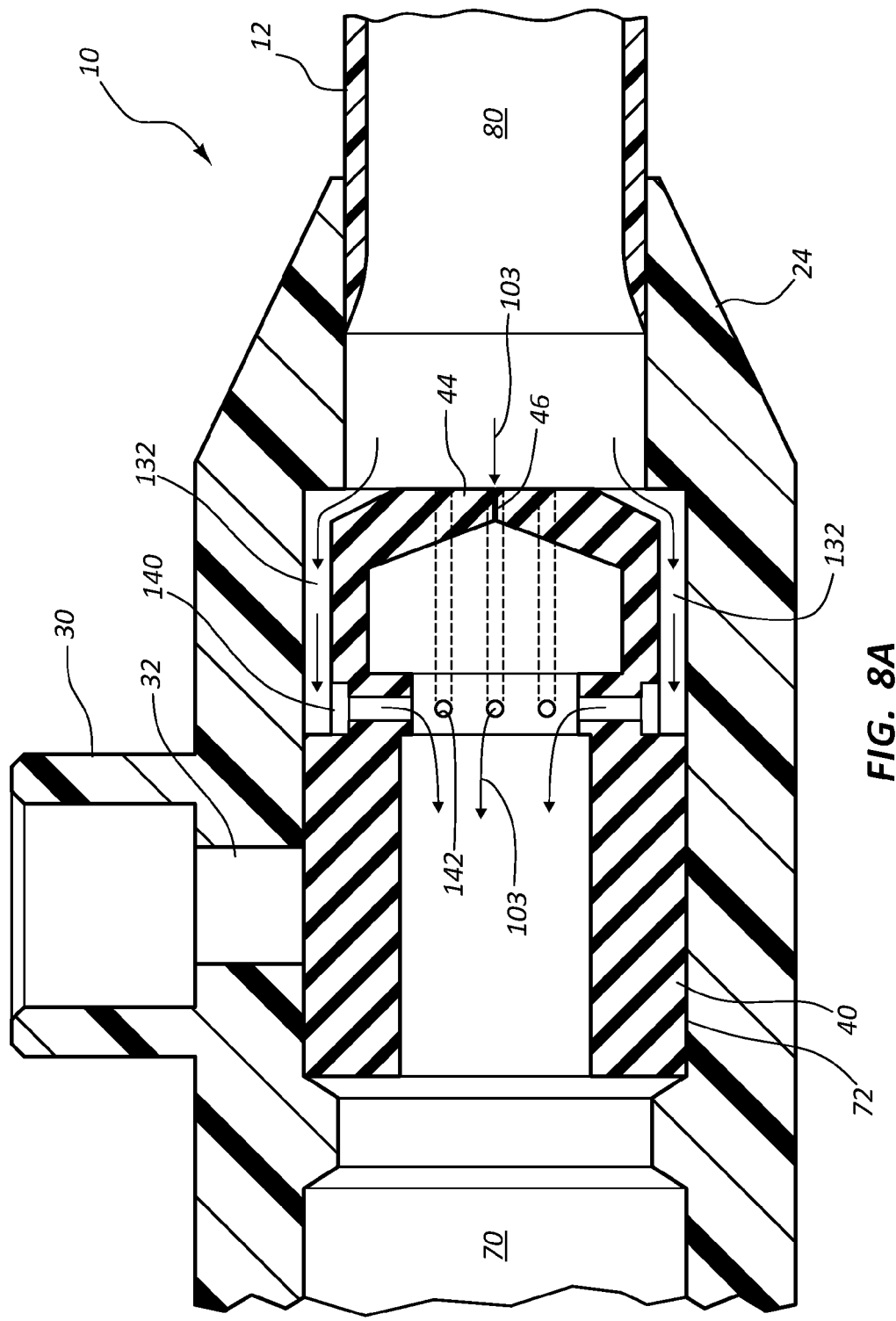
FIG. 8, shown in parts A and B, shows a cross-section side view of a vented valve in a ported catheter adapter prior to and while being injected with a fluid through the side port in accordance with a representative embodiment of the present invention.
Figure 8B:
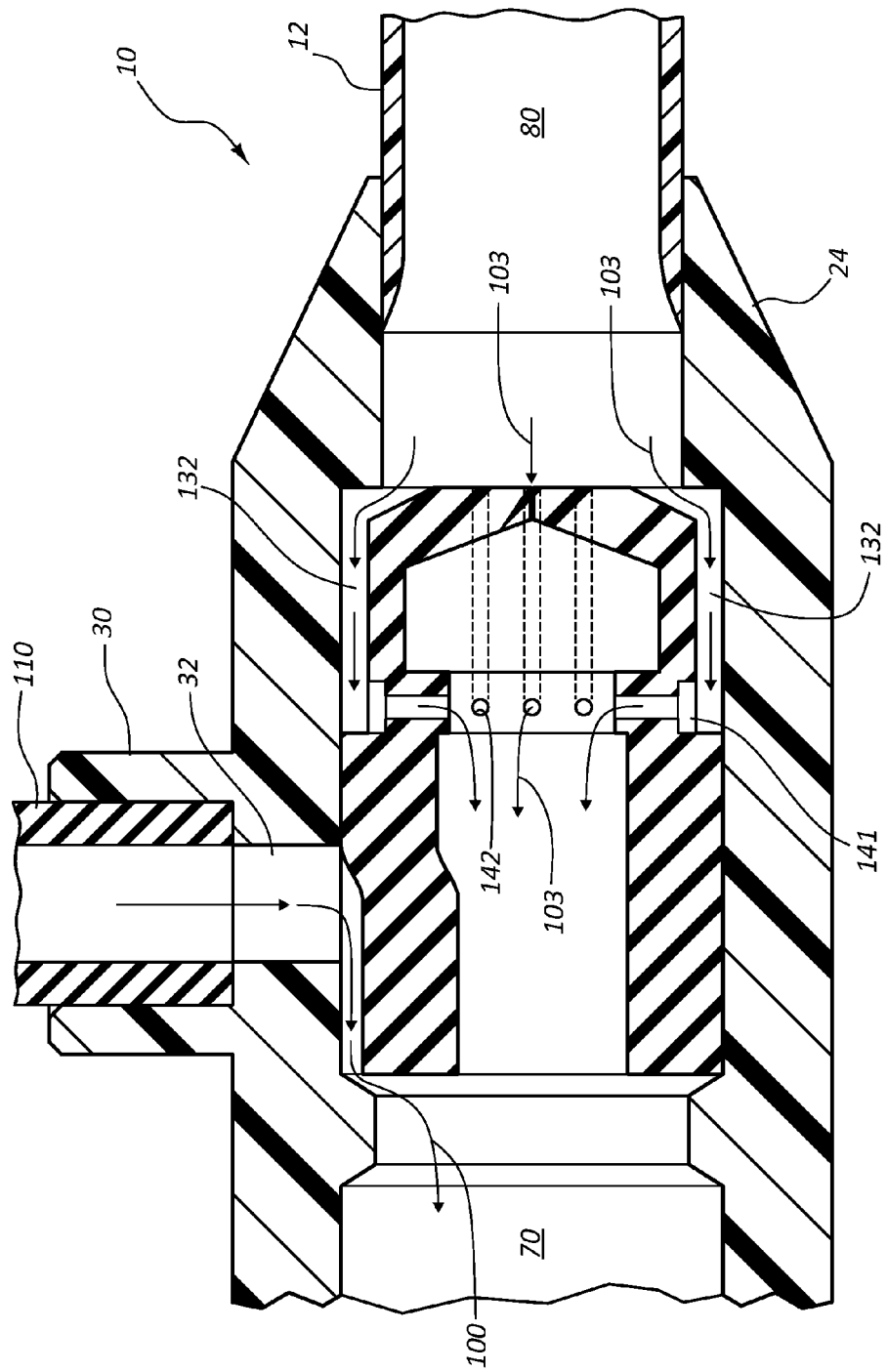

With continued reference to FIGS. 8A and 8B, in some instances vent 40 comprises an annular vent ring 141 and a plurality of vents 132 that are positioned around the entire circumference of valve 40. For these embodiments, vent ring 141 is positioned between membrane 44 and pathway 32, such that vent ring 141 does not overlap with pathway 32. As fluid 100 is injected through side port 30, the proximal end of valve 40 deforms, thereby directing the injected fluid 100 to flow in a proximal direction and into the proximal chamber 70. The distance between vent ring 141 and pathway 32 prevents fluid 100 from entering vent ring 141 and/or vents 132. Further, in some instances vent ring 141 comprises a thickened sidewall, thereby providing increased rigidity to this portion of valve 40. The thickened sidewall further prevents this portion of valve 40 from deforming when fluid 100 is injected through side port 30.

Figure 9:
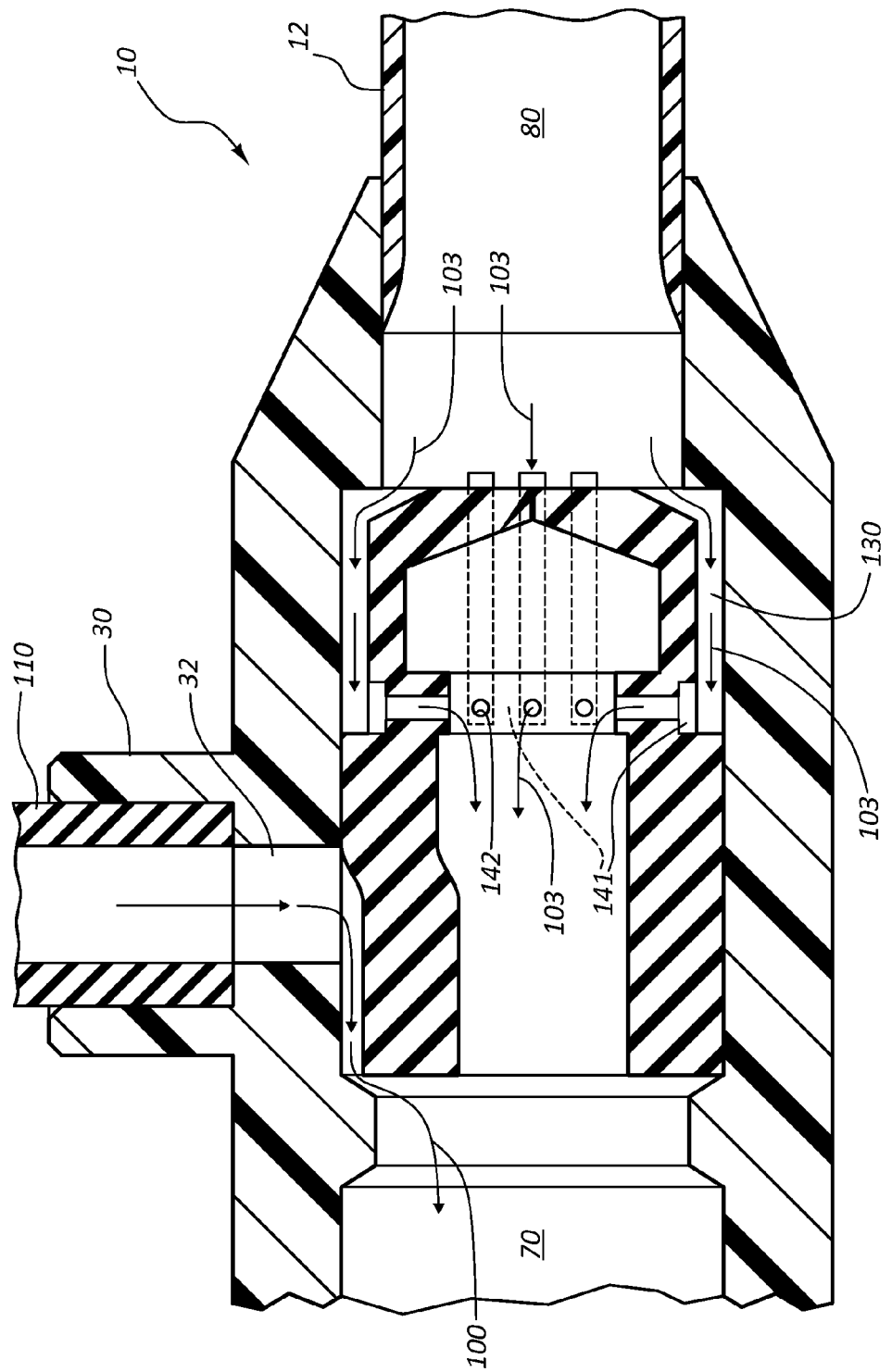
FIG. 9 shows a cross-section side view of a valve positioned in a catheter adapter having a plurality of vents and being injected with a fluid through the side port of the catheter adapter in accordance with a representative embodiment of the present invention.

In other instances, vent 130 comprises one or more horizontal grooves formed in the inner wall surface of catheter adapter 20, as shown in FIG. 9. For these embodiments, the distal opening of vent 130 is in fluid communication with distal chamber 80, and the proximal opening is in fluid communication with vent ring 141 of valve 40. In some instances, a secondary vent ring (not shown) is provided on the inner surface of catheter adapter 20, wherein venting holes 142 are not interconnected via vent ring 141, but rather are aligned with the secondary vent ring. Thus, air within vents 130 and the secondary vent ring is transferred to proximal chamber 70 via venting holes 142.

Venting holes 142 provide pathways through valve 40, thereby providing fluid communication between proximal chamber 70 and distal chamber 80 via vents 130 and vent ring 141. In some instances, the cross-section area of vents 130 is greater than the cross-section area of venting holes 142. In other instances, the cross-section area of vents 130 is the same or less than the cross-section area of venting holes 142. Vents 130 may similarly be used with a semi-annular vent ring 140, as discussed previously. Vents 130 may also be used with vents 132, as may be desired.

One having skill in the art will appreciate that the features discussed herein may equally be implemented in either the outer surface of valve 40 or the inner surface of catheter adapter 20, without requiring undue experimentation. Thus, one having skill in the art may achieve desired air flow between the proximal and distal chambers 70 and 80 of catheter adapter 20 by any combination of the features and methods discussed herein.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A ported catheter assembly, comprising:
    a catheter adapter having a proximal end, a distal end and a lumen extending therebetween, the catheter adapter further comprising a side port forming a pathway through a sidewall of the catheter adapter and in communication with the lumen;
    a valve disposed within the lumen and having a proximal opening, a distal membrane, and an inner cavity extending therebetween, the valve comprising an outer surface in contact with an inner surface of the catheter adapter, wherein a portion of the outer surface forms a seal between the lumen and the pathway of the side port, and wherein the distal membrane divides the lumen into a proximal chamber and a distal chamber; and
    a vent interposed between the outer surface of the valve and an inner surface of the catheter adapter, wherein the vent comprises a first end proximate the distal chamber and a second end disposed towards a middle portion of the valve, wherein the vent comprises a cross-sectional area that permits the passage of air and prevents the passage of blood.

2. The ported catheter assembly of claim 1, further comprising a valve actuator disposed within the proximal chamber and having a base, a tip and a body extending therebetween, the body being at least partially positioned within the inner cavity such that the tip of the valve actuator is positioned proximate to the distal membrane, and the base is positioned proximate to the proximal end of the catheter adapter.

3. The ported catheter assembly of claim 2, wherein the proximal end of the catheter adapter further comprises an opening through which the base of the valve actuator may be accessed.

4. The ported catheter assembly of claim 2, further comprising an actuator retention tab coupled to an outer surface of the valve actuator and positioned within an annular groove formed on an inner surface of the catheter adapter within the proximal chamber.

5. The ported catheter assembly of claim 4, wherein the lumen comprises a minimum diameter, the annular groove comprises a diameter that is greater than the minimum diameter, and the retention tab comprises an outer diameter that is less than the diameter of the annular groove and greater than the minimum diameter.

6. The ported catheter assembly of claim 4, wherein the annular groove comprises a first end, a second end, and a length extending therebetween, wherein the retention tab travels within the annular groove between the first and second ends to advance the tip of the valve actuator though a slit in the distal membrane of the valve.

7. The ported catheter assembly of claim 2, wherein the valve may be defeated to provide a pathway through the distal membrane by advancing the tip of the valve actuator through a slit in the distal membrane.

8. The ported catheter assembly of claim 1, wherein the valve may be defeated by injecting a fluid through the side port, whereby fluid pressure from the injected fluid temporarily deforms the body of the valve to permit the injected fluid to flow into the proximal chamber of the lumen via the pathway though the sidewall of the catheter adapter.

9. The ported catheter assembly of claim 1, wherein the vent comprises at least one of one or more recessed surfaces formed in the outer surface of the valve and one or more recessed surfaces formed in the inner surface of the catheter adapter.

10. The ported catheter assembly of claim 1, wherein the second end of the vent is disposed distal to the pathway through the sidewall of the catheter adapter.

11. The ported catheter assembly of claim 1, wherein the outer surface of the valve further comprises an annular recess or a partial annular recess in fluid communication with the vent and comprising an opening to permit fluid communication between the vent and the inner cavity of the valve via the annular recess or the partial annular recess.

12. The ported catheter assembly of claim 11, wherein the annular recess or the partial annular recess is disposed at the second end of the vent.

13. The ported catheter assembly of claim 1, wherein the cross-sectional area of the vent permits the passage of air at a desired flow rate from 0.5 ml/min to 3 ml/min.

14. The ported catheter assembly of claim 1, wherein the cross-sectional area of the vent permits the passage of air at a desired flow rate from 0.1 ml/min to 10 ml/min.

15. The ported catheter assembly of claim 1, wherein the valve comprises a flexible tube having an outer diameter that is approximately the same size as an inner diameter of the lumen, whereby the valve is retained within the lumen by an interference fit.

16. A blood control valve for use in a ported catheter adapter, the valve comprising:
    a flexible tube, comprising:
        a proximal opening;
        a distal membrane;
        an inner cavity extending between the proximal opening and the distal membrane;
        an outer surface having a diameter that is approximately equal to an inner diameter of the ported catheter adapter, whereby the valve is configured to be retained within the catheter adapter via a friction fit, the outer surface further having a length sufficient to form a seal between a lumen of the catheter adapter and a pathway of a side port of the ported catheter adapter, and wherein the distal membrane divides the lumen of the ported catheter adapter into a proximal chamber and distal chamber; and
    a recess formed in the outer surface of the flexible tube, wherein the recess comprises a first end proximate the distal chamber when the valve is inserted into the catheter adapter and a second end disposed towards a middle portion of the flexible tube, wherein the recess has a cross-sectional area that permits the passage of air and prevents the passage of blood.

17. The blood control valve of claim 16, wherein the seal may be selectively defeated by injecting a fluid through the side port, thereby temporarily permitting the fluid to flow through the pathway of the side port and into the lumen of the catheter adapter through a space provided between the outer surface of the flexible tube and an inner surface of the catheter adapter.

18. The blood control valve of claim 17, wherein the outer surface of the flexible tube further comprises a vent ring in fluid communication with the recess and comprising an opening to permit fluid communication between the vent ring and the inner cavity of the flexible tube.

\* \* \* \* \*